US00PP31311P2

(12) United States Plant Patent
Hansen

(10) Patent No.: US PP31,311 P2
(45) Date of Patent: Dec. 31, 2019

(54) **X *MANGAVE* PLANT NAMED 'DESERT DRAGON'**

(50) Latin Name: **x *Mangave* hybrid**
Varietal Denomination: Desert Dragon

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/501,029

(22) Filed: Feb. 11, 2019

(51) Int. Cl.
*A01H 5/00* (2018.01)
*A01H 6/12* (2018.01)

(52) U.S. Cl.
USPC ..... Plt./373

(58) Field of Classification Search
USPC ..... Plt./373
CPC ..... A01H 5/00; A01H 6/12
See application file for complete search history.

*Primary Examiner* — Annette H Para

(57) ABSTRACT

A new and unique x *Mangave* plant named 'Desert Dragon' characterized by a short, rounded mound of fleshy, linear to lanceolate leaves that are wavy, twisted and slightly arching margins and develop glaucous, blue-green with greyed-purple spotting with intense light. The leaves have numerous small, flexible marginal teeth pointing outwardly. The new plant is suitable for the garden or as a potted plant in the garden or home.

1 Drawing Sheet

Botanical classification: x *Mangave* hybrid;
Variety denomination: 'Desert Dragon';

STATEMENT REGARDING PRIOR DISCLOSURES UNDER 37 CFR 1.77(b)(6)

The first public disclosure of the claimed plant, in the form of a private sale, was made by Walters Gardens, Inc. on Feb. 12, 2018 to Plant Delights Nursery, Inc. Plants for this sale were obtained from the inventor. No plants of x *Mangave* 'Desert Dragon' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* hybrid plant, x *Mangave* 'Desert Dragon' that was hybridized by the inventor at a wholesale perennial nursery in Zeeland, Mich., USA as a cross between a proprietary unnamed hybrid known as 12-23-3 (not patented) as the female or seed parent times and an unreleased proprietary hybrid known as 12-6-1 (not patented) as the male or pollen parent. The cross was performed Feb. 23, 2015 and seeds were harvested and sown in the summer of 2015. Through trials at the same nursery the plant was assigned the breeder code 15-77-7. The new plant has been successfully asexually propagated by sterile shoot-tip tissue culture and by basal offsets at the same nursery in Zeeland, Mich. The asexual tissue culture propagation has been found to produce stable and identical plants that maintain all the unique characteristics of the original plant.

BRIEF SUMMARY OF THE INVENTION x *Mangave* 'Desert Dragon' differs from its parents as well as all other *Manfreda, Agave* and x *Mangave* known to the applicant. The female parent had fewer leaves per plant, broader leaves with fewer undulations per leaf, more-glaucous, less greyed purple in the foliage and the leaves are flatter and not as folded or channeled. The male parent has less purple spotting in the foliage and flat leaves. The nearest comparison plants are: 'Dreadlocks' U.S. Plant patent application Ser. No. 16/350,480, 'Catch a Wave' U.S. Plant Pat. No. 29,723, 'Falling Waters' U.S. Plant Pat. No. 30,650, 'Mayan Queen' U.S. Plant patent application Ser. No. 15/932,527, 'Silver Fox' U.S. Plant Pat. No. 29,642, and the *Agave gypsophila* grandparent (not patented). 'Dreadlocks' has leaves that are longer, more sinuate, less twisting and arching, and the main color is medium green with purple spots. 'Catch a Wave' has larger habit with fewer leaves per plant that are longer and broader and has more glaucous green foliage with smaller greyed-purple spots. 'Falling Waters' has a larger habit leaves that are more green. 'Mayan Queen' is a larger plant with broader leaves are more glaucous and more bluish colored with more intense purple spotting. 'Silver Fox' has shorter habit, the foliage is more glaucous blue, flatter with less channeling and waviness and the purple spotting is smaller. The *Agave gypsophila* grandparent has fewer, thicker and broader leaves on larger plant and the coloration is more glaucous-grey and larger and firmer teeth and terminal spines.

'Desert Dragon' is unique from all of the above cultivars and all *Agave*, x *Mangave* and *Manfreda* known to the inventor by the following combined traits:

1. Short, rounded mound of linear to lanceolate, deeply channeled, wavy, twisted, slightly arching, sarcous leaves;
2. Leaves develop large, dense, dark greyed-purple spotting on a glaucous, light greyed- purple background;
3. Leaf margins have many, small, flexible, outwardly-facing, marginal teeth;
4. Moderate growth rate;

BRIEF DESCRIPTION OF THE DRAWING

The photograph of x *Mangave* 'Desert Dragon' demonstrates the overall appearance of the new plant including the unique traits as a three-year-old plant grown in a greenhouse and moved to a full-sun trial garden in Zeeland, Mich. The colors are as accurate as reasonably possible with color reproductions. Ambient light spectrum, temperature, source and direction may cause the appearance of minor variation in color.

DETAILED BOTANICAL DESCRIPTION

Figure 1:
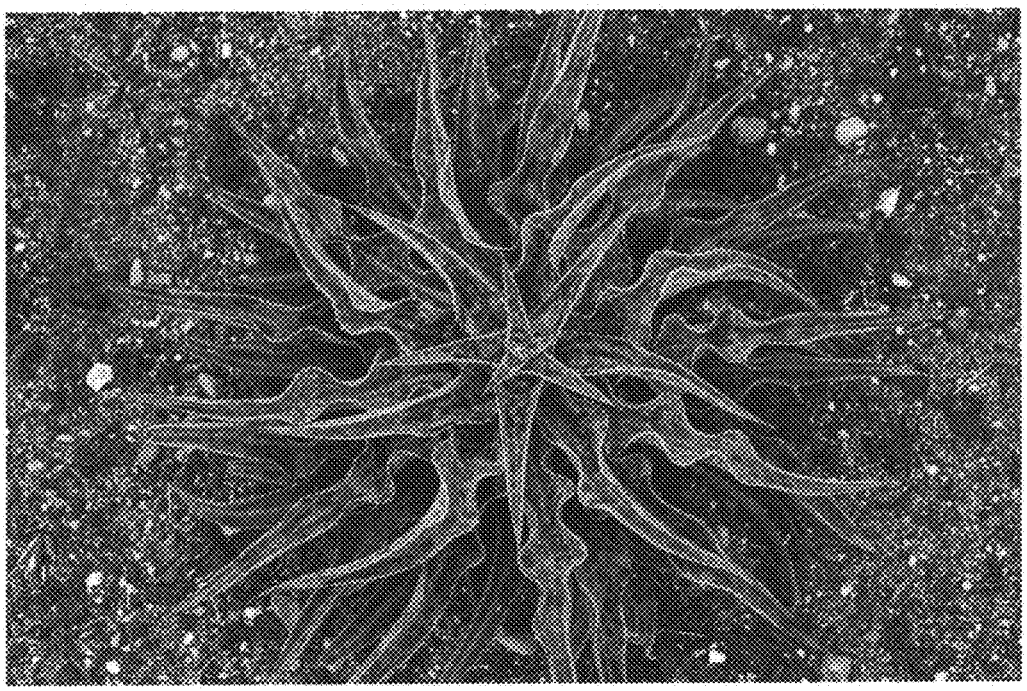
FIG. 1 shows a plant from above.
Figure 2:
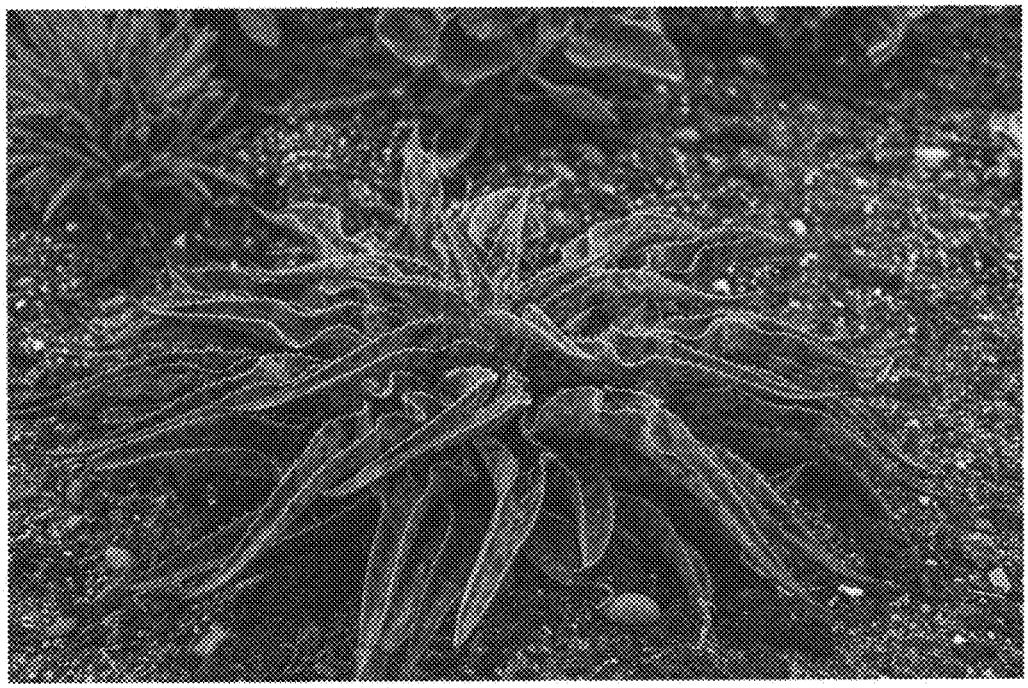
FIG. 2 shows a side view.

The following descriptions and color references are based on the 2015 edition of The Royal Horticultural Society Colour Chart except where common dictionary terms are used. The new plant, x *Mangave* 'Desert Dragon', has not been observed under all possible environments. The phenotype may vary slightly with different environmental conditions, such as temperature, light, fertility, moisture and maturity levels, but without any change in the genotype. The following observations and size descriptions are of a three-year-old plant in a commercial wholesale greenhouse in Zeeland, Mich. with supplemental water and fertilizer as needed.

Parentage: A proprietary unnamed hybrid known as 12-23-3 as the female or seed patent which contains *Manfreda maculosa, Agave gypsophila* and *Agave attenuata*; and a proprietary hybrid known as 12-6-1 as the male or pollen parent which contains 'Bloodspot' (not patented) and *Agave geminiflora;*

Propagation: By sterile shoot-tip tissue culture;

Time to initiate roots from tissue culture: About 21 days;

Growth rate: Moderate;

Crop time: About 14 to 18 weeks to finish in a 3.8 liter container from a 35 mm tissue culture growing at about 21° C.;

Rooting habit: Fleshy, lightly branching, with roots up to 30 cm long;

Root color: Nearest RHS 158B;

Plant shape and habit: Succulent herbaceous perennial with basal rosettes of about 112 leaves radially emerging outwardly from central stem, producing a radially-symmetrical, developing a rounded mound with maturity;

Plant size: Foliage height about 23.0 cm tall from soil line to the top of the leaves and about 74.0 cm wide at the widest point just above soil level;

Stem: To about 3.5 cm across; covered with foliage;

Foliage description: Linear to lanceolate; simple; sessile; bi-laterally symmetrical; sarcous; apex narrowly acute without terminal spine; base truncate; older lower leaves slightly concavo-convex and younger upper leaves flat; margins undulate, serrate with small, flexible, outwardly pointing teeth; both adaxial and abaxial glabrous and glaucous;

Apical spine: About 6.0 mm long and 1.0 mmm wide;

Marginal teeth: Small, flexible even when mature; protruding about 2.5 mm long from margin and 1.0 mm wide at base, average spacing about 3.7 mm apart;

Leaf size: To about 36.0 cm long, about 40.0 mm wide toward middle; center base about 8.0 mm thick at basal midrib; older leaves channeled to about 15.0 mm deep; average about 33.0 cm long, 36.0 mm wide and 6.0 mm thick in longitudinal center; spotted on both adaxial and abaxial vary from 1.0 mm to 9.0 mm across;

Foliage fragrance: None observed;

Leaf number: About 112 per plant before flowering;

Leaf blade color:

*Adaxial*(*low light*).—Young and mature leaves nearest RHS 137B with spots nearest RHS 139A.

*Abaxial*(*low light*).—Young and mature leaves nearest RHS N138B with spots of nearest NN137A.

*Adaxial*(*high light*).—Young leaves blend between RHS 133C and RHS N138D with spots between RHS N187A and RHS N187B; mature leaves blend between RHS N198D and RHS 122B with spotting nearest RHS N187A.

*Abaxial*(*high light*).—Young leaves blend nearest RHS N138C and RHS 133C with patches between RHS N187B and RHS N187B; mature leaves blend between RHS N198D and RHS 122B with spotting nearest RHS N187A.

*Teeth.*—Nearest RHS 155B with blush nearest RHS 186B.

*Apical spine.*—Nearest RHS N200B.

Petiole: Leaves sessile;

Veins: Parallel; not distinct abaxial or adaxial;

Flower description: Not yet observed;

Fruit and seed: Not observed;

Disease resistance: x *Mangave* 'Desert Dragon' has not been observed to be resistant to diseases beyond that which is normal for x *Mangave, Agave* or *Manfreda*. The new plant is xeromorphic and survives well with minimal water once established. The new plant is estimated to be hardy at least from USDA zone 9. Full extent of winter hardiness has not been tested.

It is claimed:

1. A new and distinct cultivar of ornamental x *Mangave* plant named 'Desert Dragon' as herein described and illustrated.

* * * * *